(12) United States Patent
Merkel et al.

(10) Patent No.: US 11,670,414 B2
(45) Date of Patent: Jun. 6, 2023

(54) PROCESS, CONTROL UNIT, COMPUTER PROGRAM PRODUCT AS WELL AS SYSTEM FOR PROVIDING FAILURE SAFETY FOR A MEDICAL MONITORING PROCEDURE

(71) Applicant: Drägerwerk AG & Co. KGaA, Lübeck (DE)

(72) Inventors: Maximilian Merkel, Hamburg (DE); Tobias Klotz, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1007 days.

(21) Appl. No.: 16/177,825

(22) Filed: Nov. 1, 2018

(65) Prior Publication Data
US 2019/0131014 A1   May 2, 2019

(30) Foreign Application Priority Data
Nov. 2, 2017   (DE) .................. 10 2017 010 150.7

(51) Int. Cl.
*G16H 40/20*   (2018.01)
*G16H 40/63*   (2018.01)
(Continued)

(52) U.S. Cl.
CPC ............. *G16H 40/20* (2018.01); *G16H 10/60* (2018.01); *G16H 40/40* (2018.01); *G16H 40/63* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 2002/0016568 A1* | 2/2002 | Lebel | A61N 1/37258 604/131 |
| 2003/0040835 A1* | 2/2003 | Ng | G16H 10/40 700/214 |

(Continued)

FOREIGN PATENT DOCUMENTS

| | | | | |
|---|---|---|---|---|
| DE | 20 2009 002 851 U1 | 7/2009 | | |
| EP | 3138488 A1 * | 3/2017 | ......... | A61B 5/0002 |

OTHER PUBLICATIONS

Michael Imhoff & Silvia Kuhls, Alarm algorithms in Critical Care Monitoring, 102 Anesthesia & Analgesia 1525-1537 (2006), https://journals.lww.com/anesthesia-analgesia/fulltext/2006/05000/Alarm_Algorithms_in_Critical_Care_Monitoring.39.aspx (last visited Jan. 5, 2023) (Year: 2006).*

*Primary Examiner* — Jason B Dunham
*Assistant Examiner* — Nicholas Akogyeram, II
(74) *Attorney, Agent, or Firm* — McGlew and Tuttle, P.C.

(57) ABSTRACT

The present invention pertains to a process for providing failure safety for a medical monitoring procedure (40) of patient data (41), wherein the medical monitoring procedure (40) is carried out by a standard computer (10), wherein the patient data (41) are sent, furthermore, to the standard computer (10) and are compared with threshold values there. The present invention further pertains to a control device (20), to a computer program product (30) as well as to a system (1) for providing failure safety for a medical monitoring procedure (40) of patient data (41), wherein the medical monitoring procedure (40) is carried out by a standard computer (10).

20 Claims, 1 Drawing Sheet

Figure 1:
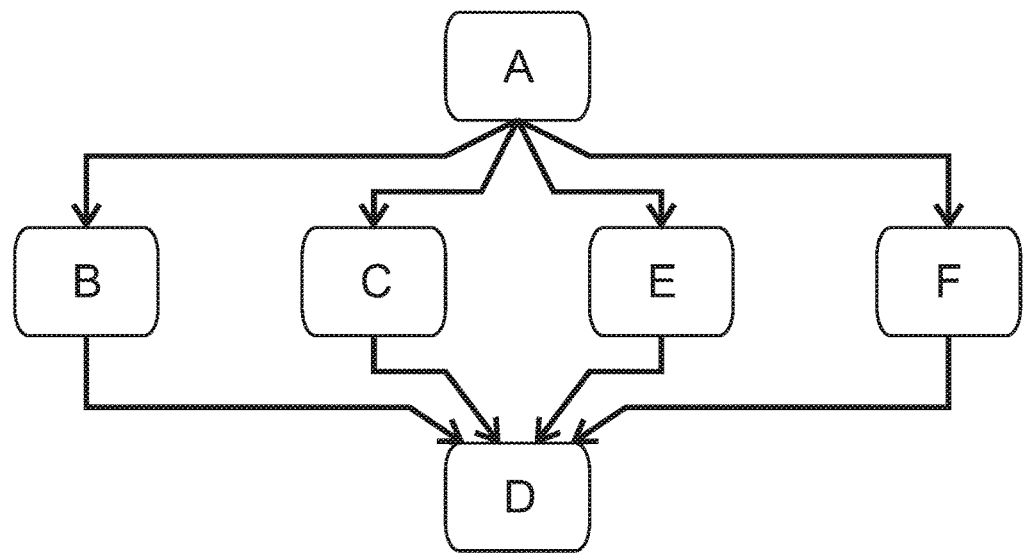

(51) Int. Cl.
*G16H 10/60* (2018.01)
*G16H 40/40* (2018.01)
*G16H 80/00* (2018.01)

(56) References Cited

U.S. PATENT DOCUMENTS

| | | | | |
|---|---|---|---|---|
| 2006/0059253 | A1* | 3/2006 | Goodman | G06Q 10/06 709/223 |
| 2006/0173260 | A1* | 8/2006 | Gaoni | A61B 5/0022 600/365 |
| 2011/0068929 | A1* | 3/2011 | Franz | A61B 5/746 340/573.1 |
| 2011/0128146 | A1* | 6/2011 | Hsueh | G16H 40/67 340/539.12 |
| 2013/0267795 | A1* | 10/2013 | Cosentino | A61B 5/746 600/301 |
| 2015/0031962 | A1* | 1/2015 | Chang | A61B 5/0022 600/301 |
| 2015/0095054 | A1* | 4/2015 | Kaigler | G16H 40/67 705/2 |
| 2016/0117461 | A1* | 4/2016 | Yeh | G16H 40/40 705/2 |
| 2016/0224884 | A1* | 8/2016 | Gayl | G06N 5/04 |
| 2016/0346459 | A1* | 12/2016 | Chow | G16H 20/17 |
| 2017/0055890 | A1* | 3/2017 | Kube | G06F 21/6245 |

\* cited by examiner

PROCESS, CONTROL UNIT, COMPUTER PROGRAM PRODUCT AS WELL AS SYSTEM FOR PROVIDING FAILURE SAFETY FOR A MEDICAL MONITORING PROCEDURE

The present invention pertains to a process for providing failure safety for a medical monitoring procedure of patient data, wherein the medical monitoring procedure is carried out by a standard computer, wherein the patient data are sent, furthermore, to the standard computer and are compared with threshold values there. The present invention further pertains to the provision of failure safety for a medical monitoring procedure of patient data, wherein the medical monitoring procedure is carried out by a standard computer. Moreover, the present invention pertains to a computer program product for providing failure safety for a medical monitoring procedure of patient data, wherein the medical monitoring procedure is carried out by a standard computer. Another aspect of the present invention pertains to a system for providing failure safety for a medical monitoring procedure of patient data, wherein the medical monitoring procedure is carried out by a standard computer, comprising at least one control device and a computer program product.

STATE OF THE ART

It is known, in principle, in modern medical engineering that patients are monitored by apparatuses. Such a monitoring may pertain to data characterizing the status of the patient, for example, a blood pressure, a heart rate and/or an oxygen saturation in the blood of the patient. The monitoring may comprise, in particular, the triggering of alarms when the patient data being monitored exceed or drop below limit values. This is carried out essentially usually by the monitoring apparatuses themselves, which are arranged in the vicinity of the patient bed.

To provide for a monitoring of a plurality of patients, it is, furthermore, known from the state of the art that monitoring procedures of, for example, a plurality of patients may also be combined and carried out by means of suitable computer program products on standard computers. Centralized monitoring of a plurality of patients can be provided in this manner. However, the fact that standard computers do not have a sufficient failure safety was found to be disadvantageous in connection with the use of standard computers. In particular, if failure of a component of the standard computer develops unnoticed, this may cause the entire monitoring procedure of the patient data to be compromised, so that the patient's wellbeing and the patient's safety may be jeopardized. As a second aspect, it was, furthermore, found to be problematic in connection with the use of standard computers that these are often provided in a great variety of configurations. It is therefore impossible comprehensively to ensure that the monitoring procedures are carried out uniformly and especially identically on all standard computers. In particular, the output of alarms, for example, in case the patient data being monitored drop below or exceed threshold values, often cannot be ensured or can be ensured only incompletely at best. In particular, a special output of standard alarms in case of special events, for example, of a cardiac alarm or of the oxygen saturation in the blood of the patient being monitored dropping below a limit value, often cannot be made possible or it can be made possible only incompletely at best.

Based on this state of the art, the basic object of the present invention is to at least partially eliminate these drawbacks of processes, control devices, computer program products as well as systems for providing failure safety for a medical monitoring procedure. Therefore, the object of the present invention is to provide a process, a control device, a computer program product as well as a system for providing failure safety for a medical monitoring procedure, by which the highest possible safety can be made available for a patient being monitored, wherein especially a failure of components of the standard computer or of the entire monitoring procedure can be detected with certainty and displayed to a user by an alarm.

DISCLOSURE OF THE INVENTION

The above object is accomplished by a process for providing failure safety for a medical monitoring procedure of patient data with the features of the independent claim 1. Further, the object is accomplished by a control device having the features of the coordinate claim 11, by a computer program product having the features of the coordinate claim 16 as well as by a system having the features according to the coordinate claim 17. Further features and details of the present invention appear from the subclaims, the description and the drawings. Features and details that are described in connection with the process according to the present invention also apply, of course, in connection with the control device according to the present invention, with the computer program product according to the present invention as well as with the system according to the present invention and vice versa, so that reference is and can always mutually be made concerning the different aspects of the present invention.

According to a first aspect of the present invention, the object is accomplished by a process for providing failure safety for a medical monitoring procedure of patient data, wherein the medical monitoring procedure is carried out by a standard computer, wherein the patient data are further sent to the standard computer and are compared with threshold values there. A process according to the present invention is characterized by the following steps:

a) Data-communicating connection of an external control device with the standard computer,
b) determination and checking of a functional status of the standard computer by a control device,
c) determination and checking of a functional status of the control device by the standard computer, and
d) output of an alarm signal by the control device in the presence of at least one incorrect functional status detected in steps b) and/or c).

A process according to the present invention is configured such as to provide failure safety for a medical monitoring procedure or at least to markedly improve it. Failure safety in the sense of the present invention may already be provided, in particular, by a user of the medical monitoring procedure being informed of a possible failure or of an incorrect behavior of the monitoring procedure with certainty and in time. Such a monitoring procedure is carried out, for example, as a computer program product on a standard computer. Patient data, comprising, for example, data of a blood pressure, a cardiac function, a lung function or the like, are sent to the standard computer in a wireless and/or wired manner in a data-communicating manner. These patient data are compared in the monitoring procedure with threshold values in order to detect a change, especially an exacerbation, of the health status of the patient being monitored. A patient, but especially also a plurality of patients, can be monitored by such a monitoring procedure.

To ensure the monitoring of these patients, it is especially essential that the monitoring procedure and especially the standard computer function flawlessly. This can be made possible and ensured by a process according to the present invention, which will be described below.

An external control device is connected to the standard computer in a data-communicating manner in a first step a) of a process according to the present invention. This may preferably take place, for example, via a standard interface, for example, a USB interface. The control device thus represents an additional building block, which is provided separately from the standard computer, but connected to this in a data-communicating manner. The control device itself may further have, in particular, a fail-safe configuration, for example, by the use of especially robust and stable components and/or due to the presence of a separate power supply, especially also of an independent power supply, for example, a rechargeable battery or a capacitor.

In the next step b), a functional status of the standard computer is now determined and checked by the control device. The determination of a functional status in the sense of the present invention may comprise especially a detection of data of the standard computer, for example, a temperature of components of the standard computer, fan speeds and/or data that pertain to the function of additional hardware components of the standard computer, for example, of a hard drive, of a central processor core and/or of data interfaces. By checking these determined data of the functional status, it can be determined or detected by the control device whether the functional status of the entire standard computer is within preset parameters, as a result of which the presence of an incorrect functional status can be detected with certainty.

The functional status of the control device is determined and checked in step c) of a process according to the present invention, which is preferably carried out simultaneously with the above step. This determination and checking of the functional status of the control device may also comprise data on components of the control device, for example, of a processor core of the control device, of data interfaces of the control device or the like. These data may, in turn, be checked by the standard computer, especially in order to determine whether the control device operates within preset parameters. On the whole, it can thus be ensured in this step c) that the functional status or the operation of the control device is also within preset parameters, as a result of which an incorrect state of the control device can likewise be detected with certainty.

Provisions are made, in particular, in the last step d) of a process according to the present invention, for an alarm signal being outputted by the control device in the presence of an error in at least one of the determined functional states of both the standard computer and the control device. It can be displayed with certainty in this manner to a user of the standard computer, on which the monitoring procedure is carried out, that at least one of the components being used has a functional status that is incorrect. However, reliable performance of the monitoring procedure cannot be guaranteed any longer with such a component having an incorrect functional status. Due to a user of the standard computer being informed, he can thus be enabled, in particular, to interrupt the monitoring procedure on this special standard computer in order to rule out jeopardizing the safety of the patient.

In summary, provisions can thus be made by a process according to the present invention for providing or enhancing the failure safety of a medical monitoring procedure of patient data, which is carried out by a standard computer. In particular, a user of the standard computer can be informed with certainty if an incorrect functional status of at least one of the installed components is present, regardless of whether the component in question is the standard computer or the control device. Steps b) and c) provide, in particular, a redundant checking of the functional status of both the standard computer and the control device, so that an incorrect functional status of one of these two components can be detected with certainty.

A process according to the present invention may especially preferably be perfected such that at least one of the following steps is additionally carried out, and an alarm signal is outputted by the control device in the presence of at least one incorrect functional status detected in steps e) and/or f):

e) Determination and checking of a functional status of the standard computer by the standard computer, and f) determination and checking of a functional status of the control device by the control device.

Provisions may further be made in this especially preferred embodiment of a process according to the present invention for the standard computer and/or for the control device also being subjected itself to a checking for its own functional status. A further increase in redundancy can be provided in this manner when checking the functional status of the individual components, which participate in the operation of checking patient data. Failure of one of the components can thus be detected with an even higher certainty and displayed to the user of the standard computer.

Moreover, provisions may be made in a process according to the present invention for steps b) and/or c) and/or e) and/or f) to be carried out simultaneously or at least essentially simultaneously and/or continuously or at least essentially continuously. By carrying out these steps simultaneously, it can be ensured, in particular, that all the incorrect functional states occurring will be detected rapidly and especially immediately. By carrying out these steps continuously, an especially rapid detection of an incorrect functional status of one of the components used can be determined [sic—performed—Tr.Ed.] immediately. Essentially simultaneously or continuously can be defined in the sense of the present invention especially such that the individual steps are carried out in relation to a cycle of the processor cores of the standard computer and of the control device simultaneously or continuously.

Moreover, provisions may be made in the process according to the present invention for an alarm signal to be outputted by the standard computer in case of a failure of the control device in step d). The circumstance that the control device is often no longer able to output an alarm signal in case of its complete failure is taken into consideration in this embodiment of a process according to the present invention. This can, however, usually be detected by the standard computer, and it can be compensated by the output of the alarm signal by the standard computer itself. A user of the standard computer can thus be reliably informed of the presence of an incorrect functional status, especially of the control device, even in case of a complete failure of the control device.

A process according to the present invention may also be configured such that a functional status of a software environment and/or a functional status of a hardware environment of the standard computer are determined and checked in step b) and/or step e). A software environment may comprise, in particular, an operating system of the standard computer, driver, a data communication from or to the standard computer or the like. A hardware environment is defined in the sense of the present invention as comprising everything that is installed as elements or components in the standard computer, especially a central processor core, drives, memory components, output devices and/or interfaces. In particular, the certainty of finding an incorrect functional status of the entire standard computer can be increased by checking both the software environment and the hardware environment in respect to their respective functional status.

Provisions may further also be made in the process according to the present invention for a functional status of a software environment ["eine" on 1. 21, p. 8 is a typo for "einer"—Tr.Ed.] and/or for a functional status of a hardware environment of the control device to be determined and checked in step c) and/or step f). A software environment may comprise an operating system of the control device, driver, a data communication or the like concerning the control device as well. Moreover, the control device may also have components installed as hardware environment, for example, a central processor core, memory components, interfaces or the like. Safety can also be increased in respect to the control device by determining and checking both a functional status of the software environment and a functional status of the hardware environment to the effect that an incorrect functional status of the entire control device can be determined with certainty and detected immediately.

Further, provisions may be made in a process according to the present invention for the control device to be used for outputting alarms of the medical monitoring procedure in case the patient data drop below and/or exceed a threshold value. In particular, the control device may especially preferably be configured to output standardized alarms in these cases. A uniform and especially standardized alarm generation environment can be provided in this manner by the use of a process according to the present invention with such a control device, especially independently from the standard computer being used. A user can thus be informed concerning the monitoring procedure by always the same alarms independently from the standard computer being used, as a result of which the safety of the patients can be increased on the whole.

Provisions may further be made especially preferably in the process according to the present invention by additionally determining and checking a functional status of the medical monitoring procedure in step b) and/or step e). In particular, a functional status of the standard computer is determined and checked in steps b) and e). In a preferred embodiment of a process according to the present invention, this is expanded to the effect that a functional status of the medical monitoring procedure itself is determined and checked in addition to the basic functional status of the standard computer. In other words, provisions may be made in this manner for also determining and checking the function of the monitoring procedure in respect to specified parameters when a process according to the present invention is being carried out. Not only the platform, i.e., the standard computer, on which the monitoring procedure is carried out, but the monitoring procedure itself are thus also subjected to checking. The patient's safety can be further increased in this manner in respect to the failure of the monitoring procedure.

A process according to the present invention may be perfected especially preferably to the effect that test data are generated for the monitoring procedure for checking the functional status of the medical monitoring procedure, wherein a monitoring result of the monitoring procedure, which result is elicited by the test data, is detected and analyzed by the control device in step b) and/or by the standard computer in step e). The fact that values of the monitoring result can be determined in advance as a response of the monitoring procedure to the test data generated by the control device and are thus known can be utilized here, in particular. An incorrect behavior of the monitoring procedure can thus be detected with certainty by a comparison of the monitoring result with these known responses. An incorrect functional status of the monitoring procedure itself can be detected in this manner especially rapidly and with certainty. In particular, this may also be carried out before the monitoring procedure proper of actual patient data is started. A test run of the entire monitoring procedure already before the putting into operation with patient data can be made possible in this manner.

Further, provisions may also be made in the process according to the present invention for the result of the monitoring performed by the standard computer in step c) and/or step e) to be determined and checked by the control device. An additional redundancy can be provided in this manner in the mutual checking of the control device and of the standard computer. The results determined by the standard computer concerning a functional status of both the control device and the standard computer are checked again by the control device in this preferred embodiment of a process according to the present invention. The safety of an error-free functional status of the entire standard computer and of the control device can be further increased by this additional level of checking.

According to a second aspect of the present invention, the object is accomplished by a control device for providing failure safety of a medical monitoring procedure of patient data, wherein the medical monitoring procedure is carried out by a standard computer. A control device according to the present invention is characterized in that the control device is configured for use in a process according to the first aspect of the present invention. All the advantages that were described in reference to a use of a control device according to the present invention according to the second aspect of the present invention in a process according to the present invention according to the first aspect of the present invention can thus also be provided by a control device according to the present invention according to the second aspect of the present invention, which is used in such a process according to the first aspect of the present invention.

A control device according to the present invention may also be configured such that the control device has a standard interface, especially a USB interface, for the data-communicating connection of the control device with the standard computer. Such a standard interface is especially preferred because a corresponding standard counter interface is present at most standard interfaces. A data-communicating connection of the control device with the standard computer can be made possible in this manner in an especially simple manner. In particular, a physical standard interface, for example, a plug and/or a cable, is preferred to a wireless interface, because data transmission between the control device and the standard computer can be made possible hereby with even more certainty.

A control device according to the present invention may also be configured such that the control device has an alarm generation unit for sending alarm signals. This alarm generation unit may especially preferably be configured for sending acoustic alarm signals. Sending of optical, haptic or data communication-based alarm signals may be provided as well. An especially wide variety of alarm generations can be provided for a user in this manner by a control device according to the present invention.

A control device according to the present invention may especially preferably be perfected such that the alarm generation unit has a fail-safe configuration, wherein the alarm generation unit has, in particular, an emergency power supply. It can be ensured, in particular, by such a fail-safe configuration of the alarm generation unit that it is still possible, at least at the beginning, to output an alarm signal at least in the overwhelming majority of cases even in case of total failure of the control device. An emergency power supply represents an especially preferred type of embodiment for the fail-safe configuration of an alarm generation unit. Such an emergency power supply may be formed, for example, by a capacitor and/or an electric battery.

A control device according to the present invention may also be perfected such that the alarm generation unit is configured to output standardized alarms of the medical monitoring procedure. It can be made possible in this manner in an especially simple manner that a standardized alarm environment can be provided for the user, especially concerning the patient data being monitored by the monitoring procedure. The same alarm or the same alarm environment can thus be provided for the user especially independently from the standard computer in the presence of critical states of the patient. An increase in the safety of the patient can also be achieved in this manner.

According to a third aspect of the present invention, the object is accomplished by a computer program product for providing failure safety for a medical monitoring procedure of patient data, wherein the medical monitoring procedure is carried out by a standard computer, wherein the computer program product is configured for use in the standard computer and is configured for carrying out, at least partially, a process in accordance with the first aspect of the present invention. All the advantages that are described in detail in reference to the at least partial performance of a process in accordance with the first aspect of the present invention can thus also be provided by a computer program product according to the third aspect of the present invention, which is configured for the at least partial performance of a process in accordance with the first aspect of the present invention.

According to a fourth aspect of the present invention, the object is accomplished by a system for providing failure safety for a medical monitoring procedure of patient data, wherein the medical monitoring procedure is carried out by a standard computer, comprising at least one control device and a computer program product. A system according to the present invention is characterized in that the control device is configured according to the second aspect of the present invention and the computer program product is configured according to the third aspect of the present invention. Both the control device according to the second aspect of the present invention and the computer program product according to the third aspect of the present invention are configured such that they are configured at least partially for carrying out a process according to the present invention in accordance with the first aspect of the present invention. All the advantages that were described in reference to a control device according to the present invention in accordance with the second aspect of the present invention and in reference to a computer program product according to the present invention in accordance with the third aspect of the present invention may thus also be provided by a system according to the present invention in accordance with the fourth aspect of the present invention, because the system according to the present invention in accordance with the fourth aspect of the present invention is likewise configured as a result for carrying out a process according to the present invention in accordance with the first aspect of the present invention.

Further actions improving the present invention appear from the following description of exemplary embodiments of the present invention, which are shown in the figures. All the features and/or advantages appearing from the claims, the description and the drawings, including structural details and arrangements in space, may be essential for the present invention both in themselves and in the different combinations. Components having the same function and mode of operation are provided with the same reference numbers in the drawings. In the schematic drawings, FIG. 1 shows a process according to the present invention, and FIG. 2 shows a system according to the present invention.

FIG. 1 shows a process according to the present invention, wherein steps a) through f) are designated each by capital letters. FIG. 2 shows a system 1 according to the present invention, which is configured for carrying out such a process. Both FIGS. 1 and 2 will therefore be described together below, and reference will be made to the individual figures correspondingly.

Figure 2:
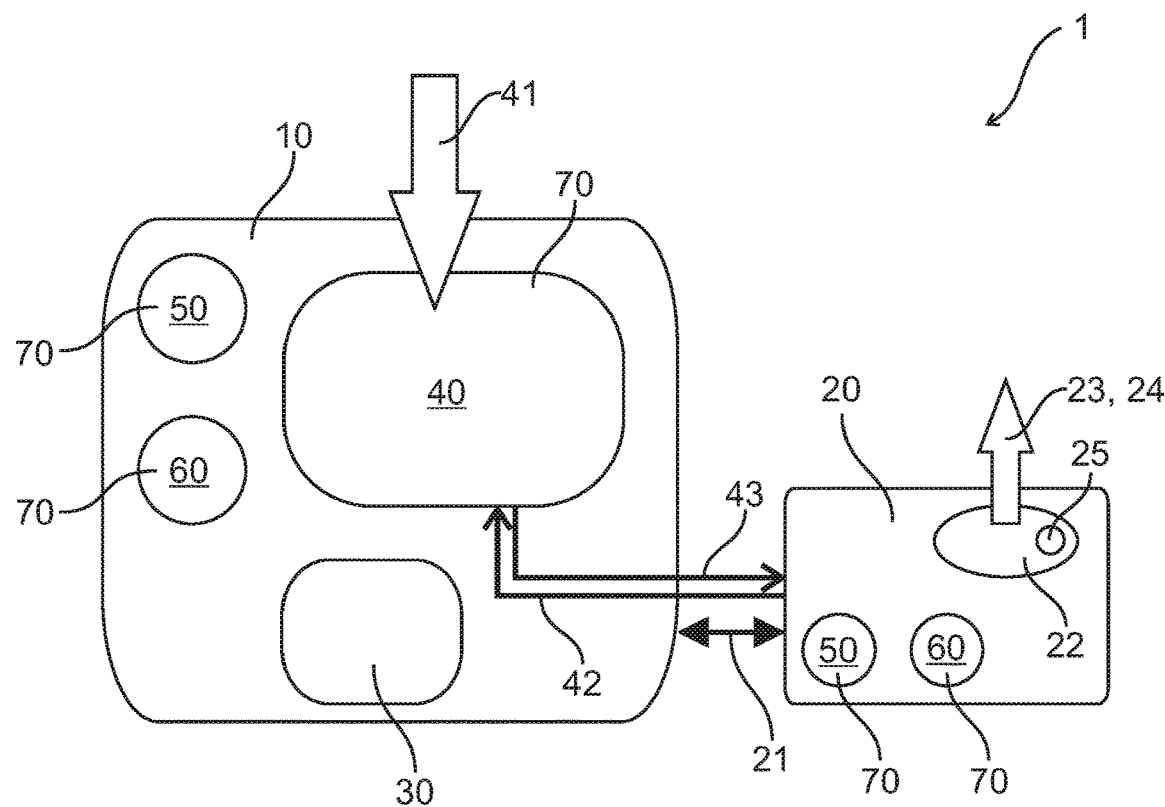

FIG. 2 shows a system 1 according to the present invention, which is configured especially for providing failure safety for a medical monitoring procedure 40, which is carried out by a standard computer 10. The monitoring procedure 40 may be carried out, for example, as a separate program on the standard computer 10. The monitoring procedure 40 receives patient data 41, for example, from one patient, but especially from a plurality of patients, and compares these with threshold values in order to determine changes in the health status of the particular patient over time. Should the patient data 41 drop below or exceed a threshold value, an alarm 24 is outputted by the monitoring procedure in order to inform a user of a system 1 according to the present invention or of the monitoring procedure 40 of this.

Failure safety of this monitoring procedure 40 can now be provided by a system 1 according to the present invention, especially by carrying out a process according to the present invention. A system 1 according to the present invention has for this purpose especially a control device 20 as well as a computer program product 30. The process according to the present invention is carried out, in particular, by the control device 20 and the computer program product 30. The control device 20 is connected for this purpose with the standard computer 10 in a data-communicating manner in a first step a), designated by A in FIG. 1. The control device 20 has especially a standard interface 21 for this, which may especially preferably be configured as a USB interface. A redundant determination and checking of a respective functional status 70 of components of the system 1 as well as of components participating in the monitoring procedure 40 is carried out now in steps b), c) and especially preferably e) and f), designated by B, C, E and F in FIG. 1. The checked principal components are the standard computer 10 as well the control device 20. A respective functional status 70 each of both the software environment 50 and of the hardware environment 60 can be determined and checked in both cases. The functional status 70 of the standard computer 10 can be determined and checked by the control device 20 in step b) of a process according to the present invention, the functional status 70 of the control device 20 can be checked in step c) by the standard computer 10, the functional status 70 of the standard computer 10 can be checked in step e) by the standard computer 10 itself, and the functional status 70 of the control device 20 can be checked in step f) by the control device 20 itself. Four determinations and checks of the functional status 70 are thus performed in this especially preferred embodiment of a process according to the present invention, especially preferably simultaneously and/or continuously, and the standard computer 10, provided especially by the computer program product 30, and the control device 20 always mutually monitor each other and themselves concerning the presence of an incorrect functional status 70. In addition, the results of the monitoring carried out by the standard computer 10 in steps c) and e) are determined once again and checked once again by the control device 20. Should the presence of an incorrect functional status 70 be determined in one of the checks performed in step b), c), e) and/or f) or in one of the checks performed additionally by the control device 20, an alarm signal 23 is outputted by the control device 20 in the last step d) of a process according to the present invention, designated by D in FIG. 1. Should the control device 20 have suffered a total failure, this alarm signal 23 can also be outputted by the standard computer 10 in step d) (not shown). On the whole, a failure of one of the two components, both the standard computer 10 and the control device 20, can be detected in this manner with certainty by a process according to the present invention and displayed to a user rapidly and unambiguously. The monitoring procedure 40 should be stopped in this case with this standard computer 10 and continued on another, functioning standard computer 10.

According to a preferred variant of a process according to the present invention, provisions may furthermore be made for a functional status 70 of the monitoring procedure 40 itself to be checked during the carrying out of a process according to the present invention. This may be carried out, for example, already by the computer program product 30 itself. Test data 42, which are sent to the monitoring procedure 40, may, for example, also be generated by the control device 20. The monitoring procedure 40 will process these data 42 as patient data 41 and then generate a monitoring result 43. This monitoring result 43 may be analyzed, as is shown, in the control device 20, for example, by a comparison with stored results, which should be elicited by the test data 42 as the monitoring result 43 in case of a functioning monitoring procedure 40. This checking may also be carried out by the computer program product 30 as part of the standard computer 10. Provisions can be made in this manner, in particular, for also making it possible for a system 1 according to the present invention to detect an incorrect behavior or an incorrect functional status 70 of the monitoring procedure 40 with certainty.

Provisions may, moreover, also be made for the control device 20 to be configured to output alarms 24, which are triggered by the monitoring procedure 40, if it is detected that the patient data 41 drop below or exceed threshold values. In particular, these alarms 24 may be standardized alarms 24, so that a standardized alarm environment with alarms 24 that are always the same can be provided for a user of such a monitoring procedure 40, regardless of the particular standard computer 10 that is used for the monitoring procedure 40 and was perfected into a system 1 according to the present invention by using a control device 20 and loading a computer program 30.

LIST OF REFERENCE NUMBERS

1 System
10 Standard computer
20 Control device
21 Standard interface
22 Alarm generation unit
23 Alarm signal
24 Alarm generation
25 Emergency power supply
30 Computer program product
40 Monitoring procedure
41 Patient data
42 Test data
43 Monitoring result
50 Software environment
60 Hardware environment
70 Functional status
A Data-communicating connection
B Determination and checking of a functional status of the standard computer by the control device
C Determination and checking of a functional status of the control device by the standard computer
D Output of an alarm signal
E Determination and checking (E) of a functional status of the standard computer by the standard computer
F Determination and checking of a functional status of the control device by the control device

What is claimed is:

1. A process for providing failure safety for a patient data medical monitoring procedure carried out by a computer, the method comprising the steps of:
   sending patient data to the computer;
   comparing data received at the computer with threshold values at the computer;
   providing a data-communicating connection of an external control device with the computer;
   determining and checking a functional status of the computer by the control device;
   determining and checking a functional status of the control device by the computer; and
   outputting an alarm signal by the control device in a presence of at least one incorrect functional status detected in the step of determining and checking a functional status of the computer and/or in the step of determining and checking a functional status of the control device.

2. A process in accordance with claim 1, further comprising the steps of:
   determining and checking a functional status of the computer by the computer;
   determining and checking a functional status of the control device by the control device; and
   outputting an alarm signal, by the control device, in the presence of at least one incorrect functional status detected in the step of determining and checking a functional status of the computer by the computer and in the step of determining and checking a functional status of the control device by the control device.

3. A process in accordance with claim 2, wherein the step of determining and checking a functional status of the computer by the control device and the step determining and checking a functional status of the control device by the computer and determining and checking a functional status of the computer by the computer and determining and checking a functional status of the control device by the control device are carried out simultaneously or at least essentially simultaneously and/or continuously or at least essentially continuously.

4. A process in accordance with claim 1, wherein the step of determining and checking a functional status of the computer by the control device and the step determining and checking a functional status of the control device by the computer are carried out simultaneously or at least essentially simultaneously and/or continuously or at least essentially continuously.

5. A process in accordance with claim 1, wherein an alarm signal is outputted by the computer in case of a failure of the control device, the step of determining and checking the functional status of the computer by the control device including a detection of data associated with at least one component of the computer and determining whether the data associated with the computer is within preset parameters, the step of determining and checking the functional status of the control device by the computer comprising a detection of data associated with at least one component of the control device and determining whether the data associated with the control device is within preset parameters.

6. A process in accordance with claim 1, wherein a functional status of a software environment and/or a functional status of a hardware environment of the computer are determined and checked in the step of determining and checking a functional status of the computer by the control device.

7. A process in accordance with claim 2, wherein a functional status of a software environment and/or a functional status of a hardware environment of the computer are determined and checked in step of determining and checking a functional status of the computer by the control device and/or in the step of determining and checking a functional status of the computer by the computer.

8. A process in accordance with claim 1, wherein a functional status of a software environment and/or a functional status of a hardware environment of the control device are determined and checked in the step of determining and checking a functional status of the control device by the computer.

9. A process in accordance with claim 2, wherein a functional status of a software environment and/or a functional status of a hardware environment of the control device are determined and checked in the step of determining and checking a functional status of the control device by the computer and/or in the step of determining and checking a functional status of the control device by the control device.

10. A process in accordance with claim 1, wherein the control device is used to output alarms of the medical monitoring procedure in case the patient data drop below and/or exceed a threshold value.

11. A process in accordance with claim 2, wherein a functional status of the medical monitoring procedure is additionally determined and checked in the step of determining and checking a functional status of the computer by the control device and/or in the step of determining and checking a functional status of the computer by the computer.

12. A process in accordance with claim 11, wherein:
test data are generated by the control device for the monitoring procedure for checking the functional status of the medical monitoring procedure; and
a monitoring result of the monitoring procedure, which result is elicited by the test data, is determined and analyzed by the control device in the step of determining and checking a functional status of the computer by the control device and/or in the step of determining and checking a functional status of the computer by the computer.

13. A process in accordance with claim 2, wherein the results of monitoring performed by the computer in the step of determining and checking a functional status of the control device by the computer and/or the step of determining and checking a functional status of the computer by the computer is determined and checked by the control device.

14. A process in accordance with claim 1, wherein the patient data monitoring procedure is carried out by the computer with a computer program product configured for use with the computer and configured for at least partially carrying out the process steps.

15. A control device for providing failure safety for a patient data medical monitoring procedure, wherein the medical monitoring procedure is carried out by a computer which receives patient data and compares data received at the computer with threshold values at the computer, the control device comprising:
a data-communicating connection with the computer, wherein the control device is configured to:
determine and check a functional status of the computer;
interact with the computer to allow a determining and checking of a functional status of the control device by the computer; and
output an alarm signal in a presence of at least one incorrect functional status detected in the determining and checking of a functional status of the computer and/or in determining and checking a functional status of the control device.

16. A control device in accordance with claim 15, wherein the data-communicating connection with the computer comprises a universal serial bus interface, wherein determining and checking the functional status of the computer by the control device includes a detection of data associated with at least one component of the computer and determining whether the data associated with the computer is within preset parameters, wherein determining and checking the functional status of the control device by the computer comprises a detection of data associated with at least one component of the control device and determining whether the data associated with the control device is within preset parameters.

17. A control device in accordance with claim 15, further comprising an alarm generation configured to send alarm signals.

18. A control device in accordance with claim 15, wherein the alarm generation unit comprises a fail-safe configuration comprising an emergency power supply.

19. A control device in accordance with claim 15, wherein the alarm generation unit is configured to output standardized alarms of the medical monitoring procedure.

20. A system for providing failure safety for a patient data medical monitoring procedure, the system comprising:
a computer with a computer program product, the computer being configured for carrying out the medical monitoring procedure; and
a control device comprising: a data-communicating connection with the computer, wherein the computer is configured to determine and check a functional status of the control device by the computer and wherein the control device is configured to determine and check a functional status of the computer, interact with the computer to allow a determining and checking of a functional status of the control device by the computer and output an alarm signal in a presence of at least one incorrect functional status detected in the determining and checking of a functional status of the computer and/or in determining and checking a functional status of the control device.

* * * * *